US008663235B2

(12) United States Patent
Tassignon

(10) Patent No.: US 8,663,235 B2
(45) Date of Patent: Mar. 4, 2014

(54) BAG-IN-THE-LENS INTRAOCULAR LENS WITH REMOVABLE OPTIC

(76) Inventor: Marie-José B. Tassignon, Berchem-Antwerpen (BE)

(*) Notice: Subject to any disclaimer, the term of this patent is extended or adjusted under 35 U.S.C. 154(b) by 862 days.

(21) Appl. No.: 11/110,463

(22) Filed: Apr. 20, 2005

(65) Prior Publication Data

US 2005/0187623 A1    Aug. 25, 2005

(51) Int. Cl.
*A61F 9/013*    (2006.01)

(52) U.S. Cl.
USPC ............................................. 606/107

(58) Field of Classification Search
CPC ................... A61F 9/00754; A61F 2009/0089
USPC ............. 623/6.16–6.17, 6.39–6.43, 6.46–6.49
See application file for complete search history.

(56) References Cited

U.S. PATENT DOCUMENTS

| | | | | |
|---|---|---|---|---|
| 4,124,905 A * | 11/1978 | Clark | | 623/6.12 |
| 5,026,396 A * | 6/1991 | Darin | | 623/6.41 |
| 5,135,530 A * | 8/1992 | Lehmer | | 606/107 |
| 5,275,624 A * | 1/1994 | Hara et al. | | 623/6.41 |
| 5,569,280 A * | 10/1996 | Kamerling | | 606/166 |
| 5,697,973 A * | 12/1997 | Peyman et al. | | 623/6.26 |
| 6,027,531 A | 2/2000 | Tassignon | | |
| 6,319,282 B1 * | 11/2001 | Nishi | | 623/6.39 |
| 6,413,276 B1 | 7/2002 | Werblin | | |
| 6,537,317 B1 | 3/2003 | Steinert et al. | | |
| 6,576,012 B2 | 6/2003 | Lang | | |
| 6,881,225 B2 | 4/2005 | Okada | | |
| 2004/0106929 A1 * | 6/2004 | Masket | | 606/107 |

FOREIGN PATENT DOCUMENTS

| | | | | |
|---|---|---|---|---|
| DE | 35 03 690 C1 * | 11/1986 | | A61F 2/16 |
| EP | 0 337 390 A2 * | 10/1989 | | A61F 2/16 |
| FR | 2 855 745 A1 * | 12/2004 | | A61F 9/007 |
| GB | 2 215 076 A  * | 9/1989 | | A61F 2/16 |
| RU | 2 066 149 C1 * | 9/1996 | | A61F 2/16 |

OTHER PUBLICATIONS

Tassignon et al., J Cataract Refract Surg, vol. 28, Jul. 2002, pp. 1182-1188.*
De Groot et al., J Cataract Refract Surg, vol. 31, Feb. 2005, pp. 398-405.*
Tassignon et Al., Bag-in-the-lens implantation of intraocular lenses, J. Cataract Refract Surg 2002; vol. 28 pp. 1182-1188.
DeGroot et Al., Effect of bag-in-the-lens implantation on posterior capsule opacification . . . , J. Cataract Refract Surg 2005; vol. 31 pp. 398-405.

* cited by examiner

*Primary Examiner* — David H Willse

(57) ABSTRACT

This invention describes a simple intraocular lens (IOL) design with a removable optic, which can be inserted in and removed from a haptic device. In this haptic the anterior and posterior capsules are sealed in order to have a perfect control over the lens epithelial cell proliferation which is thereby restricted to the peripheral part of the capsular bag. Additionally, a ring caliper is described as new surgical device to allow a precise sizing and centration of the anterior capsulorhexis. The removable optic allows repeatable correction of the eye focusing over time in case the optical parameters of the eye have changed due to a variety of factors. By separating the optic part from the haptic part, the optic part can easily be manufactured in any shape matching the optical errors of the eye, including the ocular aberrations. The optic part can be manufactured out of any biomaterial restoring ocular accommodation. The optic part may include prismatic, astigmatic or magnification correction to improve visual performance. The optic part may consist of or include an electronic device for the purpose of artificial vision.

2 Claims, 3 Drawing Sheets

Prior Art

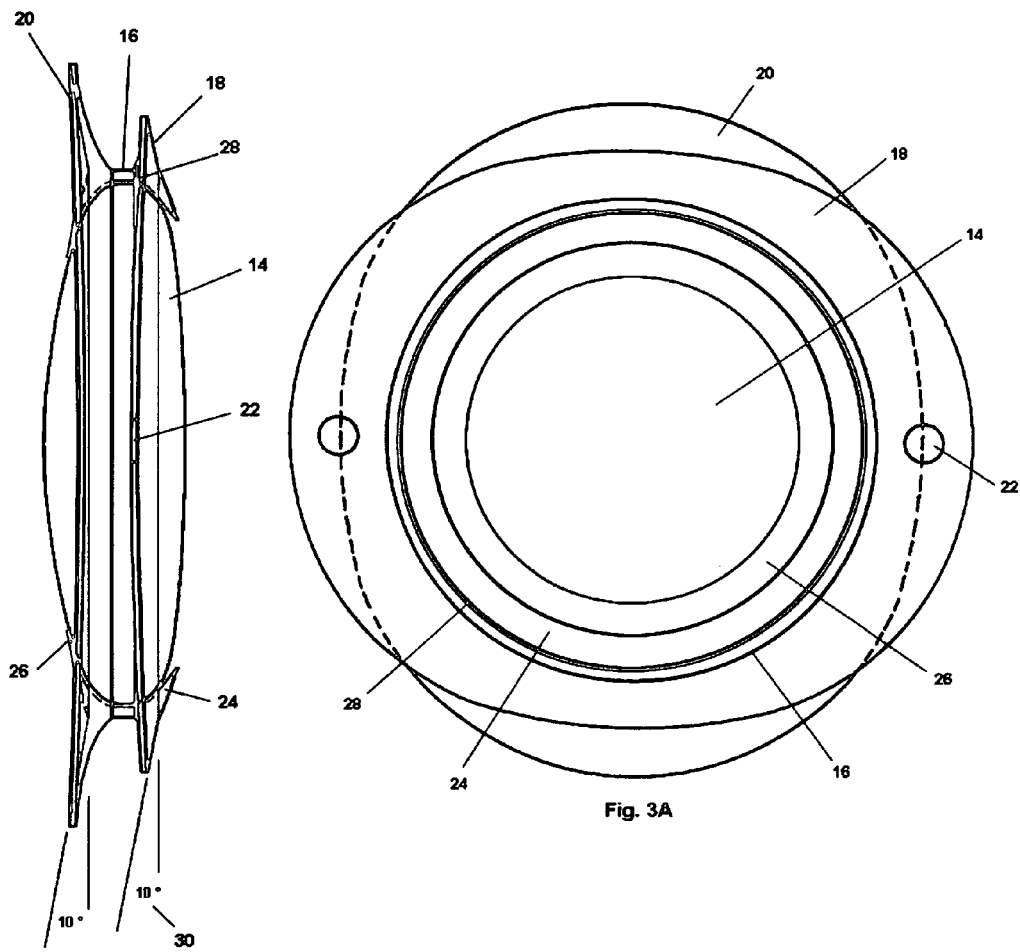
Fig. 3A
Fig. 3B
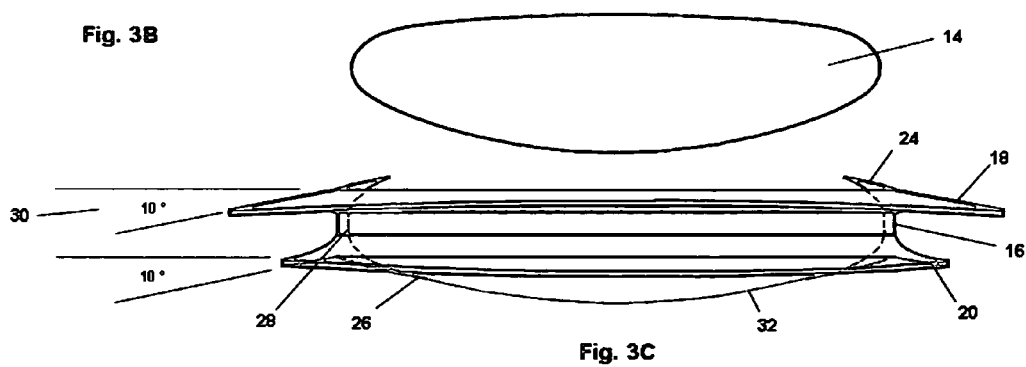
Fig. 3C

BAG-IN-THE-LENS INTRAOCULAR LENS WITH REMOVABLE OPTIC

RELATED US PATENTS AND APPLICATIONS

This application is related to U.S. patent application Ser. No. 08/950,290, filed Oct. 14, 1997, now U.S. Pat. No. 6,027,531, issued Feb. 22, 2000, and entitled Intraocular lens and method for preventing secondary opacification.

BACKGROUND OF THE INVENTION

In our U.S. Pat. No. 6,027,531 a description is made of a new concept of intraocular lens, implantable in the eye to replace the natural crystalline lens. This IOL is inserted in a calibrated, circular and continuous anterior and posterior capsulorhexis, of which the diameters are slightly smaller than the optical diameter of the lens in order to fit tightly in the groove defined at the periphery of the optical part by two flanges (one flange is the continuation of the anterior part of the optic and the other flange is the continuation of the posterior part of the optic). The perpendicularly oriented axes of the flanges facilitates the insertion of both anterior and posterior capsule into the groove by the surgeon and stabilize and avoid tilting of the IOL.

The IOL as described in U.S. Pat. No. 6,027,531 is being manufactured by the company Morcher, Germany. The intraocular lens has been implanted in children (7 months of age to 15 years), in young adults (16 to 21 years) and in about 200 adult eyes at this moment with a follow-up period of at least 5 years. The results of the clinical work and experience have been published and those publications are herewith incorporated by reference:

Tassignon M. J., De Groot V., Vrensen G. F. J. M. (2002). Bag-in-the-lens implantation of intraocular lenses. J. Cataract Refract. Surg. 28 (7), 1182-1188

De Groot V., Tassignon M. J., Vrensen G. F. J. M. (2005). Effect of bag-in-the-lens implantation on posterior capsule opacification in human donor eyes and rabbit eyes. J. Cataract Refract. Surg. 31 (2), 398-405

These publications corroborate our hypothesis as stated in the U.S. Pat. No. 6,027,531 that secondary cataract is avoided in 100% of the cases. Secondary cataract is the most frequent complication corresponding to posterior capsule opacification (PCO) in eyes operated with the traditional lens-in-the-bag implantation technique.

Besides the long-lasting excellent optical results of 100% transparency and besides the excellent stability of the lens within the eye, the bag-in-the-lens presents the additional option to be positioned electively within the eye by the surgeon. The idea of elective positioning or centration according to a visual axis of the eye of an intraocular lens, has not yet been described.

Since the publication of the U.S. Pat. No. 6,027,531, other authors have used the idea to fixate the IOL using the posterior capsule (Okada Kiyashi, U.S. Pat. No. 6,881,225), but the design is very complicated and the implantation is based on the lens-in-the-bag technique having the permanent risk that lens epithelial cells will encapsulate the IOL with proliferative tissue.

Furthermore, a large number of proposals have been made to correct the eye optics for far and for near at the time of cataract surgery. A binocular lens system was proposed by Robert Steinert (U.S. Pat. No. 6,537,317) and Lang Alan (U.S. Pat. No. 6,576,012), aiming at allowing far and near vision simultaneously. However, these IOLs are composed of two optic portions that still have the risk of cellular deposits and proliferation between the parts.

Additionally, in order to correct the optical aberrations of the eye Theodore Werblin (U.S. Pat. No. 6,413,276) proposed a three-part IOL of which at least one part can be removed and adapted according to the ocular aberrations and repositioned in a second surgical step. This elaborated IOL also has the risk of cellular deposits at the level of the interfaces causing visual impairment with over time.

OBJECTS AND ADVANTAGES OF THE INVENTION

This invention concerns an improvement of the U.S. Pat. No. 6,027,531 in two major aspects: a new device is proposed to perform easily a calibrated, circular and continuous anterior capsulorhexis, and an intraocular lens is proposed with a removable optic. Some additional minor improvements in embodiments and surgical technique are also described.

I. Device for Anterior and Posterior Capsulorhexis Size Calibration and Positioning To do so, a ring of 0.25 mm diameter, made of PMMA, or of any other biomaterial with memory, has been designed (FIG. 2). This ring can be inserted within the eye through a very small corneal or limbal incision (3 mm or less). Because of its memory, the ring will unfold within the eye as soon as inserted in the anterior chamber. It then will be gently applied on top of the anterior lens capsule and fixed with viscoelastics. The capsulorhexis can subsequently be initiated and the surgeon will take care to follow the internal border of the ring caliper. This ring caliper has two functions: (1) To determine a precise diameter of the anterior capsulorhexis. This can be achieved by manufacturing a ring with a precise internal diameter. (2) The ring is also to be used in order to center the position of the anterior capsulorhexis according to the pupillary area, or to the limbus or to any other reference used to optimize centration of the anterior capsulorhexis along an optical axis of the eye (line of sight, visual axis or other axis). The optical axis can be determined according to well-established techniques described in clinical psychophysics handbooks.

II. Intraocular Lens with a Removable Optic

Starting from the initial concept of a one piece IOL (FIGS. 1 A, B and C of the Prior Art), the haptic device can be separated from the optic part (FIGS. 3 A, B and C). This removable and replaceable optic can be versatile in design construction and incorporate spherical, astigmatic or prismatic powers as well as customized adaptive optics correction. In addition electro-optical constructions for artificial vision or low vision purposes can be incorporated. In general such optic part can be made to resemble more the natural lens of the human eye, including its GRIN properties and furthermore such design is much easier for the manufacturer to produce.

Additional advantages of such removable optic include (1) intraocular correction of ametropia repeatable over time in case the axial length or corneal optical parameters have changed due to disease, age or trauma or miscalculated previous IOL power, (2) to introduce new biomaterials in the future with additional characteristics, (3) easy access for the retinal surgeon in case of complex repeat posterior segment surgeries.

The haptic device can be constructed from an opaque material to minimize intraocular scattering and glare.

DESCRIPTION OF THE DRAWINGS

FIG. 3 A, B, C illustrate the removable optic and the haptic device as two separate parts of the new IOL. The haptic device still consists of the outer flanges (18 and 20) defining the external lens groove (16) to accommodate the anterior and posterior capsule, but in addition presents internal flanges (24 and 26) defining an internal groove (28) in order to accommodate the removable optic part of the lens (14). This modification of the original lens will allow the removal of the optic part of the lens without removing the haptic device. The external outer flanges (18-20) can be angulated posteriorly (30) compared to the straight insertion of the internal flanges of the haptic device (24-26). The posterior internal flanges (26) can extend further to create an additional closed transparent and thin barrier (32) between the removable optic and the vitreous in case posterior luxation of the removable optic is feared.

REFERENCE NUMERALS IN DRAWINGS

Figure 1A:
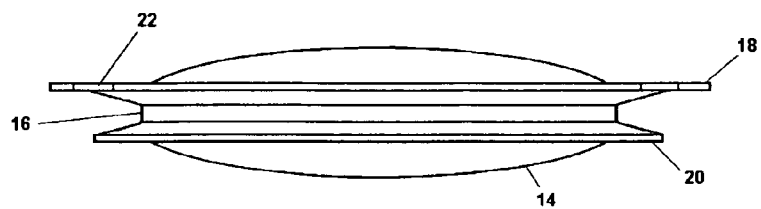
FIG. 1 A, B, C correspond to the prior art as described in U.S. Pat. No. 6,027,531. These figures illustrate the bag-inthe-lens in one piece comprising the optical part 14, the haptic parts 18 and 20 and the groove 16 to accommodate both the anterior and posterior capsule.

14 removable optic part of the intraocular lens. This part is joined with the haptic device in one piece in FIG. 1 A, B, C; and it is a separate part, removable and replaceable in FIG. 3 A, B, C
16 external groove in the haptic device to accommodate both capsules
18 anterior flange of the external part of the haptic device
20 posterior flange of the external part of the haptic device
22 perforation within the anterior flange for purpose of rotation during surgery
24 anterior flange of the internal part of the haptic device
26 posterior flange of the internal part of the haptic device
28 internal groove in the haptic device to accommodate the optic
30 angulation of the external flanges of the haptic device
32 extension of the posterior internal flange of the internal haptic device, create a membrane like barrier between vitreous and removable optic part

DESCRIPTION OF PREFERRED EMBODIMENTS

Figure 1B:
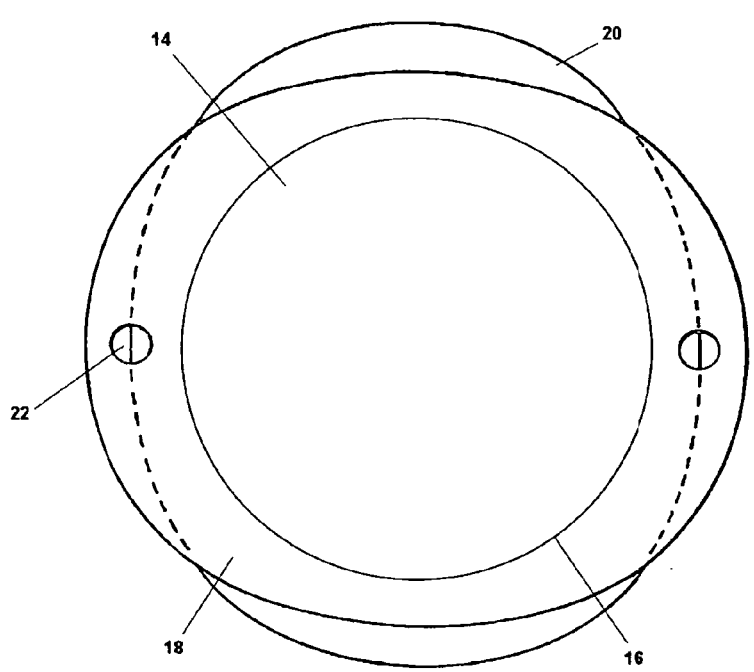
Figure 1C:
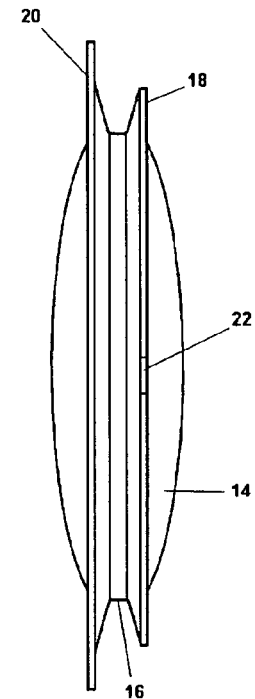

FIGS. 1 A, B and C shows the preferred embodiment of the prior art. This preferred embodiment could be slightly adapted by introducing a posterior angulation 30 of the external flanges of the haptic device. This is done in order to prevent capture of the iris into the groove immediately post-operatively. The posterior angulation will optimally vary from 5 degrees to 10 degrees. Other angulations are possible.

Figure 2:
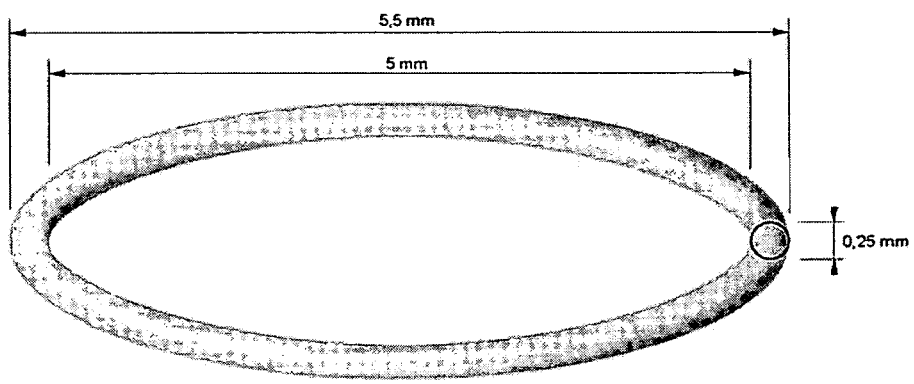
FIG. 2 illustrates the ring caliper device.

FIG. 2 shows the preferred embodiment of the ring caliper that permits a precise sizing and centration of the anterior capsulorhexis. This ring caliper may be constructed of any biomaterial allowing its insertion within the eye in a folded condition after which it will unfold in the eye to its original shape because of material memory. The diameter of the cross section of this ring is optimally 0.25 mm but can be made thinner or thicker depending on the biomaterial used. It can be transparent or colored to enhance visibility once put in place in the eye. When used in relation with an IOL of 5 mm diameter optic part size, as described in the U.S. Pat. No. 6,027,531 or in current application, a diameter of 5 mm is optimal (FIG. 2). Though this ring can be made of any diameter depending on the size of the optic part of the lens to be implanted. This ring can also be used when implanting the more traditionally lens-in-the-bag IOLs.

FIGS. 3 A, B and C show the preferred embodiment of the new intraocular lens design consisting of two separate parts: a haptic device and a removable and replaceable optic part. The haptic device is preferably made of one piece and can be made of rigid or deformable biomaterials such as silicone polymeric materials, acrylic polymeric materials, hydrogel forming polymeric materials and mixture of these materials or the like. This haptic device can be made opaque by coloration or using mechanical techniques. The aim of making the haptic part partially or totally opaque is avoiding stray light effects and glare.

The haptic device consists of an external anterior flange 18 and an external posterior flange 20, defining an external groove 16 in between. Both external flanges are made oval in shape to promote a good insertion and fixation of the intraocular lens, but can have any shape that may improve IOL fixation or insertion. Both flanges can have a variety of functional extensions or perforations 22 to promote the stability of the lens or to prevent any type of luxation or inadvertent capture of the iris. On the internal side, the haptic device has an anterior internal flange 24 and a posterior internal flange 26 defining an internal groove 28 to accommodate the removable optic part. The diameter of the internal groove can be variable but should not be less than 5 mm for reasons of optical quality and for ease of centration. The internal flanges are preferably transparent but can also be made opaque. In case a posterior luxation of the optic part into the vitreous would be an issue, the posterior internal flanges can be made continuous, 32, defining a membrane like transparent barrier between the optic part and the vitreous. The distance between the internal groove and the external groove will determine the thickness and therefore the stability and rigidity of the haptic device. This parameter can vary depending on the biomaterials used in constructing the haptic device.

The preferred embodiment of the optic part 14 is circular but of variable shape depending on the intended optical errors to be corrected, including the ocular aberrations, in particular spherical aberration or chromatic aberration. It can be made of the same biomaterial as the haptic device as specified above or can be made of another biomaterial. It can be made of one biomaterial, can use a combination of different layered biomaterials, or be made of a GRIN substance. Each construction has specific optical and mechanical properties in order to correct the spherical, the cylindrical or the toric refractive errors of the eye, and to permit accommodation (mechanically or optically mediated accommodation). Prismatic effects could be of use in relocating the preferential retinal locus of fixation in macular disease. The optic part can consist of or include an electronic device for the purpose of artificial vision or of magnification of the image on the retina for low vision purposes. These additions can be fitted on the anterior surface of the optic part, within the optic part or on the posterior surface of the optic part. The final result is a customized optic part of one piece, containing all optical adaptations needed to correct the optical errors of the eye as measured preoperatively. This one piece optic part 14 may have the same diameter as the diameter of the internal groove 28 or it can be slightly larger or it can be slightly smaller. For the purpose of stability, a slightly larger diameter of the optic part 14 could be beneficial, though a slightly smaller diameter of the optic part 14 might increase the chance of being able to use any residual accommodative effects in the eye.

DESCRIPTION OF A PREFERRED SURGICAL PROCEDURE

The surgical procedure consists of a number of steps that are currently used in conventional extracapsular cataract extraction, some of which have to be modified, and some new steps are necessary to insert the new intraocular lens in the most optimal fashion.

The opening of the anterior chamber and the filling of the anterior chamber with viscoelastics are well known steps in the prior art. The anterior curvilinear continuous capsulorhexis must be calibrated in such way that its diameter is slightly smaller (about 1 mm) than the diameter of the optic part 14.

For this purpose, the ring caliper is inserted, either by means of two forceps or by means of a lens manipulator. After insertion the ring is gently pushed on top of the anterior capsule by means of additional viscoelastics. A small opening is made in the center of the anterior capsule, which serves as the starting point for the capsulorhexis. The surgeon will take care to follow the internal border of the ring caliper.

The centration of the capsulorhexis with respect to such landmarks as the pupil edge or the limbal edge can be done using well-known techniques for documenting the optical, visual axis or line of sight. To reference the center of positioning of the ring during surgery, a standard fiduciary reticule can be used with the operating microscope.

After the anterior capsulorhexis is performed, the lens consisting of nucleus and cortical material is removed in the usual manner for an extracapsular cataract extraction technique. The posterior curvilinear continuous capsulorhexis must then be executed in such way that its diameter is the same as the diameter of the anterior capsulorhexis. The openings of both anterior and posterior capsulorhexis should match each other as close as possible in size, location and centration. The technique of making the posterior capsulorhexis is the same as the one that is currently used in conventional extracapsular cataract extraction. A puncture is made in the center of the posterior capsule. The posterior capsule is then separated from the anterior hyaloid of the vitreous by injecting viscoelastic material through the puncture in the space of Berger. After this step a calibrated posterior curvilinear continuous capsulorhexis is performed by following the edge of the anterior capsulorhexis resulting in a posterior capsulorhexis of the same size than the diameter of the anterior capsulorhexis.

The insertion of the foldable haptic device of the intraocular lens using the bag-in-the-lens technique can then be applied. It is different from the conventional lens-in-the-bag insertion technique. First, the haptic is introduced into the anterior chamber of the eye. Then the posterior flange 20 of the haptic device is placed behind the rim of the opening of the posterior capsule in the space of Berger and the anterior flange 18 of the haptic device of the intraocular lens is placed before the rim of the opening of the anterior capsulorhexis.

Because the diameters of both the anterior and posterior capsulorhexis are identical but slightly smaller than the diameter of the lens groove 16, the capsular openings will be stretched when inserting the lens, thus providing a tight junction around the intraocular lens and a closed space or environment that contains the remaining proliferating epithelial cells of the lens bag.

Once the haptic device is put in place, the removable optic part which has been chosen preoperatively in such way that it will correct the optics of the eye in the most optimal way (spherical correction, astigmatism, aberrations, accommodation) can be inserted in the anterior chamber in a foldable condition and once unfolded in the eye, put in place in the empty central space of the haptic device. The viscoelastic is then removed from the anterior chamber and the anterior chamber is then closed water tight. In case the short-term postoperative refractive or optical results are not satisfactory for the patient or in case the optical properties of the eye have changed as a function of time, the optic part can be removed from the haptic and changed by an optic part matching better the optical needs of the eye. In case the visual acuity of the patient would drop dramatically over time because of irreversible retinal or optic nerve problems, the optic can be removed from the haptic and replaced by a new optic containing or consisting of magnification elements or opto-electronic elements for the purpose of magnification or artificial vision.

SUMMARY AND SCOPE

The clinical results obtained after implantation of the intraocular lens as described in the U.S. Pat. No. 6,027,531, are excellent, and even exceptional because of an incidence of zero percent Nd-Yag laser treatments after five years of implantation. The current continuing application describes new developments as a result of our experience gained over this period.

Firstly, a ring caliper is proposed in order to facilitate the surgical procedure by improving the precision of the size and centration of the anterior and posterior capsulorhexis.

Secondly, we implemented the following modifications to the bag-in-the-lens design:
   Posterior angulations of the external haptic flanges
   Converting the intraocular lens to a two component system comprising a haptic device and an optic part, which is removable and replaceable over time
   The haptic device can be rendered partially or totally opaque
   The optic part can be customized to correct various optical aberrations, permit artificial vision or low vision rehabilitation Although the above description contains many specifications, these should not be considered as limiting the scope of the invention but as merely providing illustrations of some of the presently preferred embodiments of this invention. Other embodiments on the invention, including additions, subtractions, deletions or modifications of the disclosed embodiment will be obvious to those skilled in the art and are within the scope of the following claims. As such, the scope of the invention should be determined by the appended claims and their legal equivalents.

What is claimed is:

1. A calibrating means for sizing and positioning of an anterior and posterior capsulorrhexis during an intraocular lens implantation in an eye, said calibrating means consisting of:
   a closed solid ring having an internal diameter matching the optic part of said intraocular lens while in a relaxed state, and made of flexible biomaterial that is smooth with no cutting edges and no haptic parts, of sufficient memory and predetermined cross section diameter to facilitate (a) unfolding of said ring to its original shape on the anterior capsule of said eye after introduction into the anterior chamber of said eye with the help of a separate grasping means through a corneal incision in said eye, (b) centration of said ring relative to an axis of said eye with a separate positioning means on said anterior capsule, (c) gentle pushing and stabilizing of said ring on top of the anterior capsule by viscoelastics, and (d) removal of said ring from said anterior chamber with the help of said separate grasping means after completion of said anterior capsulorhexis by another means within said ring; whereby said calibrating means centers said anterior capsulorhexis along an optical axis of said eye for said intraocular lens implantation.

2. A method for creating an anterior capsulorhexis in an eye before implantation of an intraocular lens, comprising the steps of:

creating a small opening in the cornea of said eye of equal or less than three millimeter and injection of visco-elastic substance in the anterior chamber of said eye;

inserting a loop of solid flexible biomaterial of sufficient memory and predetermined cross section diameter through said opening in said anterior chamber with a separate grasping instrument, said loop then unfolding to a circle with an inner diameter corresponding to the optic part of said intraocular lens;

adjusting the position of said loop on top of the anterior capsule of said eye to align with a chosen optical axis of said eye;

releasing said loop from said grasping instrument;

tearing the anterior capsule substantially along the inner margin of said released loop with a separate means;

removing part of said anterior capsule and said loop from said eye through said opening; whereby said loop centers and sizes said capsulorhexis along an optical axis of said eye prior to said intraocular lens implantation.

* * * * *